United States Patent [19]

Bisek et al.

[11] Patent Number: 5,306,306
[45] Date of Patent: Apr. 26, 1994

[54] METHOD FOR PERIPROSTHETIC BONE MINERAL DENSITY MEASUREMENT

[75] Inventors: Joseph P. Bisek; James A. Hanson; Richard B. Mazess, all of Madison, Wis.

[73] Assignee: Lunar Corporation, Madison, Wis.

[21] Appl. No.: 73,264

[22] Filed: Jun. 7, 1993

Related U.S. Application Data

[63] Continuation of Ser. No. 862,096, Apr. 2, 1992, abandoned, which is a continuation of Ser. No. 655,011, Feb. 13, 1991, abandoned.

[51] Int. Cl.$^5$ .................. A61F 2/28; A61B 5/00; A61B 6/00
[52] U.S. Cl. .................. 623/16; 128/653.1; 128/661.03; 378/89
[58] Field of Search .................. 623/16; 606/76–77; 128/661.03, 653.1; 378/4, 89, 90; 250/358.1

[56] References Cited

U.S. PATENT DOCUMENTS

| 4,811,373 | 3/1989 | Stein | 378/54 |
| 4,928,959 | 5/1990 | Bassett et al. | 128/25 B |
| 4,973,846 | 11/1990 | Lanza et al. | 250/385.1 |
| 5,005,195 | 4/1991 | Lanza et al. | 378/62 |
| 5,016,639 | 5/1991 | Allen | 128/653.1 |
| 5,115,394 | 5/1992 | Walters | 378/4 X |

OTHER PUBLICATIONS

Edelman, "Dual Photon Absorptiometry May Help Surgeon Match Patient, Joint Implant", O. T., Feb. 1990, p. 3.

Stulberg et al., "X-Ray Absorptiometry for Measurement of Peri-Prosthetic Bone Mineral Density", LUNAR Corporation Research Report.

The Technical Aspect of Periprosthetic Bone Mineral Density in Uncemented Total Hip Arthoplasty, B. N. Stulberg et al., International Symposium for Custom Prostheses, Chicago Ill. 1989.

Quantitation of Bone Resorption of the Proximal Femur in Total Hip Arthroplasty, C. McCarthy et al., J. Bone Min Res 5 (Supp2):S178, 1990.

Primary Examiner—Randall L. Green
Assistant Examiner—D. Willse
Attorney, Agent, or Firm—Quarles & Brady

[57] ABSTRACT

A method of evaluating bone density around a prosthesis establishes an implant boundary at the edge of the prosthesis and creates a measurement boundary displaced from this implant boundary toward the bone producing a conformed region of interest. Matched histograms of bone density in a lateral and medial such region of interest may be displayed to evaluate symmetrical stress effects. Alternatively, bone density may be displayed plotted along an axis cutting across the medial and lateral sides. Fiducial points are identified from the bone and implant morphology to ensure that either display will have a repeatable reference and hence that such displays will be directly comparable to later and earlier displays thereby aiding in the detection of bone change.

12 Claims, 6 Drawing Sheets

METHOD FOR PERIPROSTHETIC BONE MINERAL DENSITY MEASUREMENT This is a continuation of U.S. application Ser. No. 07/862,096 filed Apr. 2, 1992, now abandoned, which is a continuation of U.S. application Ser. No. 07/655,011 filed Feb. 15, 1991, now abandoned.

FIELD OF THE INVENTION

The present invention relates to the field of radiographic analysis of the human body and, in particular, to a method of measuring and displaying bone mineral density adjacent to prosthetic bone implants.

BACKGROUND OF THE INVENTION

Bone prostheses are commonly provided to patients having bone disease or injury. Such prosthetic devices are manufactured of durable materials such as metals, ceramics, or dense plastics, and are attached to the remaining bone to replace the function of defective or missing bone and joint. In a hip replacement, for example, the ball-shaped head of a femur may be replaced with a prosthetic ball attached to the proximal end of the femur by a shaft fitted within the femur shaft.

The loosening of such implants over time and with use is a significant concern. Many different techniques have been employed to try prevent such loosening. Examples include cementing the implants to the bone, the use of porous coatings on the implant to stimulate bone in-growth, and custom fit implants.

A good fit between the implant and the bone will impart a pattern of stress onto the bone which may cause it to regenerate. If the bone grows adjacent to the implant there will be less chance of loosening.

Alternatively, loss of bone around the implant may indicate poor fit between the bone and implant in certain areas and provide an early indication of future loosening or failure of the implant. For this reason, the implanted bone is often monitored after the implant is surgically implanted. Such monitoring may be performed by conventional radiographic studies, however large changes in bone density of up to 30% may be necessary before such changes become apparent on the radiograph. Preferably, digital radiographic techniques are used to provide a quantified measurement of bone density. Such techniques include dual energy x-ray absorptiometry ("DEXA") in which a measurement of bone mineral density is derived from the varying absorption of the bone of x-rays at different energies, and dual photon absorptiometry ("DPA") where a similar measurement is made using radioisotopes. Such densitometers provide quantitative in-vivo measurement of bone mineral density ("BMD"). Other digital radiographic techniques such as computed tomography ("CT") may also provide measurements of bone density, however, the metal of the prosthesis may create image artifacts in a CT image rendering the measurement of bone density in the neighborhood of the prosthesis problematic.

Conventional DEXA or DPA equipment, when used to monitor changes in bone density, may obscure subtle changes of the bone near the implant. The region of interest ("ROI") that is isolated and evaluated by such equipment may include irrelevant bone, tissue and other artifacts. Further, the ability to determine bone loss over time is limited, with such equipment, because of the difficulty in matching the data between two different measurement periods.

SUMMARY OF THE INVENTION

The present invention provides a method of evaluating bone density measurements in the neighborhood of a prosthesis. Specifically, a matrix of bone density data values is analyzed to identify the edge of the prosthetic, said edge forming an implant boundary. A measurement boundary is then created translated from the implant boundary by a predetermined distance along a translation axis to define a region of interest conforming to the shape of the implant. A plot of the bone density may be displayed based on this ROI.

One object of the invention, therefore, is to provide an accurate indication of the state of the bone immediately adjacent to the implant. The use of a conforming ROI prevents bone from outside of the implant area from influencing or obscuring the measurements of bone near the implant. The result is improved sensitivity and easier measurement.

Another object of the invention is to provide a readily reproducible measurement that may be compared to other later studies. Fiducial points may be established with respect to the bone and the implant to form a reference for the plot of bone density. The conforming ROI is referenced from the edge of the implant and the fiducial points and therefore may be accurately and repeatably located.

Plots of bone density showing the medial and lateral sides of the implant aligned in the proximal/distal direction also may be displayed simultaneously.

Yet a further object of the invention, then, is to provide a display method that highlights possible implant related bone resorption. With the medial and lateral sides of the bone measured and displayed simultaneously, symmetrical or non-symmetrical bone loss is readily apparent, such as may be caused by abnormal stress patterns from the implant.

Other objects and advantages besides those discussed above shall be apparent to those experienced in the art from the description of a preferred embodiment of the invention which follows. In the description, reference is made to the accompanying drawings, which form a part hereof, and which illustrate one example of the invention. Such example, however, is not exhaustive of the various alternative forms of the invention, and therefore reference is made to the claims which follow the description for determining the scope of the invention.

DETAILED DESCRIPTION OF THE PREFERRED EMBODIMENT

The present invention provides the ability to analyze in vivo bone mineral density within one or more regions of interest, or ROI, that conforms to the outline of the prosthesis implanted into a patient. This flexibly defined ROI, which will thus not normally be rectangular, permits critical areas of bone density to be examined free from influence by other areas and structures. The ROI may also be referenced to a fiducial point, to permit the same ROI to be evaluated by repetitive scans taken over long periods of time to generate reliably comparative values.

The values obtained from bone density measurement in the ROI may be displayed in a histogram of average or cumulative bone density values taken within as series of segments along the implant. The display of such a histogram on a CRT screen can provide to the clinician an instantaneous picture of bone density over the length of the implant. Alternatively, a profile of bone density along an individual segment may be examined to make a quantitative measurement of bone adsorption or hypertrophy in the neighborhood of the bone. Both medial and lateral histograms and profiles may be displayed simultaneously to permit the rapid identification of symmetrical effects that may indicate their origin in stress or lack of stress from the implant.

INSTRUMENT

Figure 1:
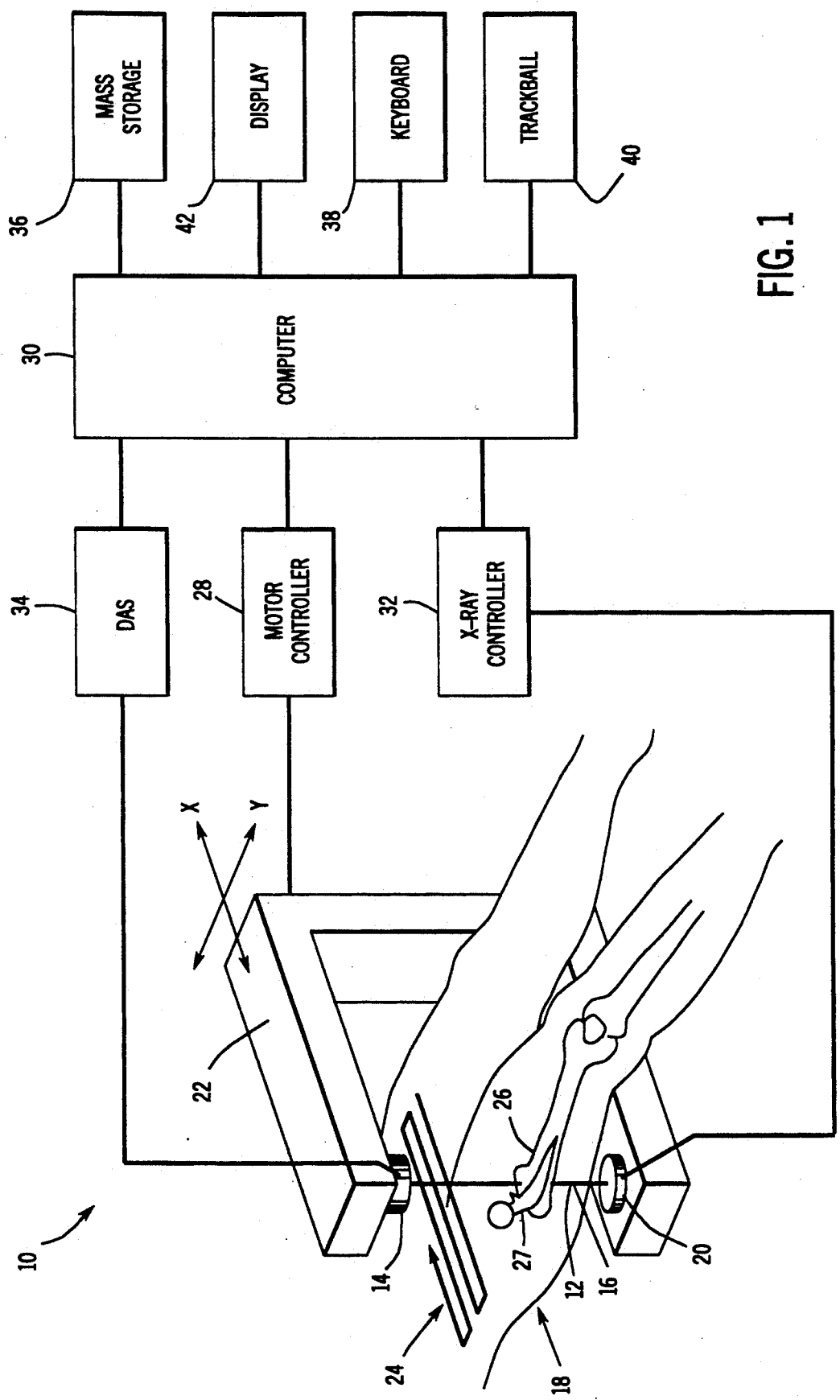
FIG. 1 is a schematic view of a dual x-ray bone densitometer suitable for collecting bone density data over a scan for use with the present invention.

Referring to FIG. 1, a bone densitometer 10, of the preferred type for use with the present invention, projects an dual-energy x-ray beam 12 from a x-ray source 14 along a ray 16 through a patient 18 to an opposed detector 20. The x-ray source 14 and detector 20 are mounted on a carriage 22 to move in unison in a raster scan pattern 24 by means of stepper or servo motor (not shown). The raster scan pattern 24 sweeps the ray 16 over a rectangular area of the patient 18 by alternately directing it along one of two perpendicular axis x, and y of a Cartesian coordinate system with the x-ray beam 12 parallel to a third orthogonal z axis.

Preferably, in the case of the evaluation of a hip implant, the carriage 22 is positioned to sweep an area including the neck and shaft of the femur 26, including the trochanter, and prosthetic implant 27. The orientation of the raster scan pattern 24 is preferably such that the shaft of the femur 26 lies substantially parallel to the y axis of the raster scan and the data is acquired in successive scan lines along the x-axis. The scanning, data analysis, and data display procedures described here may also be performed on prostheses in other parts of the body in which case the orientation, location and length of the raster scan may be suitably adjusted.

The movement of the carriage 22 is controlled by a motor controller 28 receiving signals from a computer 30. The x-ray source 14 includes an x-ray tube along with a K-edge filter to create two narrow energy bands of x-ray emissions. The signal from the detector 20 is sampled and digitized by data acquisition system ("DAS") 34 which may transmit the digitized samples to the computer 30 which stores the data in computer memory (not shown) or on mass storage device 36. An operator may provide inputs to the computer 30 by means of keyboard 38 and trackball 40 (or mouse) which allow positioning of a cursor on display screen 42 as is understood in the art. The display screen 42 also provides a means of displaying information obtained from the raster scan.

At a continuous series of discrete data points over the raster scan pattern 24, the signal from the detector 20 is sampled by the DAS 34 at each of two x-ray energy levels produced by the x-ray source 14, as filtered by the K-edge filter. Thus at each location, two samples, having values corresponding to the absorption by the patient 18 of x-rays 12 at both of the x-ray energy levels, may be collected. Each pair of samples may be identified to the x and y coordinate of the location at which the samples were acquired. Together, the sample pairs over the entire raster scan pattern form elements of a data matrix, whose matrix coordinates correspond to the ray 16 coordinates. On presently available DEXA machines, as shown in FIG. 1, a spatial resolution of 0.6 mm between samples may be obtained over a raster scan area of about 12 by 14 cm.

Figure 2:
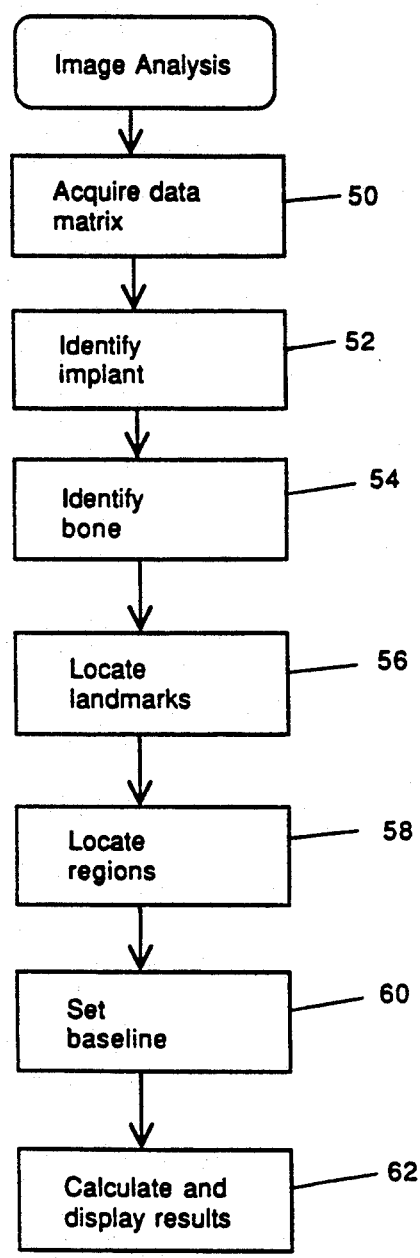
FIG. 2 is a flow chart showing the steps of separating tissue, bone, and implant and identifying fiducial points in the collected data.

Referring to FIG. 2, the acquisition of this data matrix is represented by process block 50. As is understood in the art, the sample pair taken at each of the two energy levels together provides an indication of bone density or mineral content of the bone along ray 16. The data matrix therefore represents the density of the tissue and bone over the scanned area of the patient's femur 26. It will be understood to one of ordinary skill in the art that the data matrix of bone density samples also may be obtained by other densitometers, such as those based on DPA and CT as described above. The data matrix is stored in a file on computer 30.

Image analysis

Upon completion of the acquisition of data matrix, the data elements of the matrix are analyzed to differentiate data elements associated with bone from data elements associated with tissue and the implant. This process is illustrated by the flow chart of FIG. 2, illustrating the process of image analysis, which begins with the step of acquiring the matrix of data values from the scan of the patient. Included within this step, indicated at 50 in FIG. 2, is the combining of the two values of each sample to create a non-calibrated value corresponding to the total density along the associated ray 16 of each sample. The data points thus created are referred to as PBM, for pseudo bone mineral content. The numbers are pseudo values because they are non-calibrated and therefore dimensionless. At this point in the analysis, therefore, only the relative differences between the data points are significant, not their absolute values. While the calibration for each value could be done at this point, it is consumptive of computer resources, and thus is deferred at this point, and the PBM values are used. The calibration of the final values to correspond to standard physical values is performed as a last step. This technique is well known in the art.

The remaining steps in the flowchart of FIG. 2 will be describe first in overview and then in detail. The data values of PBM are precessed at step 52 to identify the implant. Then at step 54, the values are analyzed again to identify the bone. At step 56, the bone values are again analyzed to identify the bone landmarks. Based on that analysis, the regions of interest in the bone are identified at step 58. From the analysis of those regions, baselines are derived at step 60. Finally the results are calculated and calibrated and the results are displayed at step 62.

Identify Implant

Figure 3:
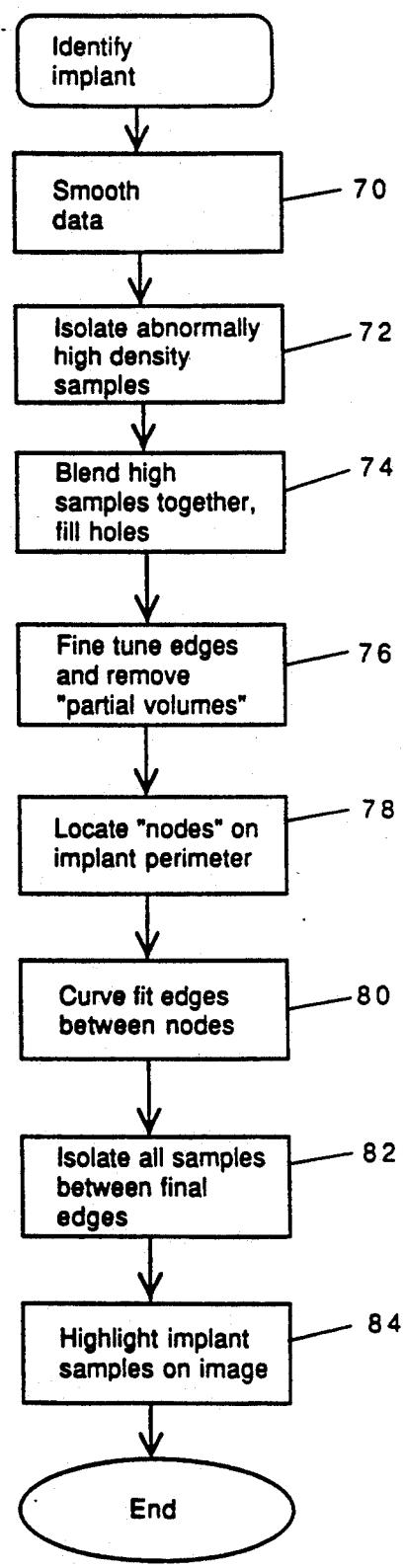
FIG. 3 is a flow chart showing the steps of the identify implant step from the flowchart of FIG. 2.

This process is intended to identify regions of the data matrix of PBM values which correspond to the physical implant. Since the values are at this point dimensionless, the analysis of the values to determine the values which correspond to the implant must be done on the basis of relative comparison of values rather than absolute values. To begin the process, which is illustrated in FIG. 3, the matrix of data values is filtered with a low band pass filter to remove high frequency noise components from the data at step 70. Next the data values must be analyzed to generally identify the area of the implant.

Expressed in absolute values, the normal biological range of bone mineral density in human femurs ranges up to values less than 3.0 grams per square centimeter. An examination of the density values of common hip implants reveals that most current implants have a density value much greater than 3.0. Thus, working with the PBM data matrix, a comparative analysis is performed to identify a region where the values are abnormally high when compared to other parts of the data matrix. This step is illustrated at 72 in FIG. 3, which illustrates the procedure for the implant identification step 52 of FIG. 2. This analysis results in the generation of a threshold value, above which all data points are defined to represent implant, and those data values are tagged by the computer as representing implant.

The next step is to fill any voids or defects in the representation of the implant. For some implants, the matrix of data values has been found to have occasional values inside the area of the implant with inappropriately low PBM values. At step 74, all data points that are surrounded on all four sides within a defined distance (5 mm) by implant are also defined to be implant. This step has the effect of filling in a solid area in the matrix as implant area. The edges of the implant area are then adjusted at step 76. The absolute edges of the implant are identified by locating the points in the data matrix at which the greatest differences exist between adjacent values. These points of greatest change are defined to be the edge of the implant. This calculated true edge is slightly extended outward in this step to compensate for shadowing or partial edge effects caused by the sharp edge. This is done by moving the defined edge outward until the change between adjacent data point values becomes almost zero. At this step in the process a rough outline of the implant exists in the matrix of values.

It is now possible to smooth out the rough outline of the implant created to this point. This step, indicated at 78 in FIG. 3, involves breaking up the identified edges of the implant into a series of small sections which are defined between "nodes." The nodes are defined to be the locations of changes in direction of the implant perimeter, such as corners. Since presently used implants are known to have certain shapes, certain nodes can be "forced" onto the data, since the system knows that a discontinuity exists in the real implant at a certain point. Then between each set of nodes thus defined a best fit curve routine is used to find a high order (fourth degree) curve which will have a best fit with the measured data to define the edge of the implant. The curves that best represent the data are then incorporated into the final outline of the implant at step 80.

Once the outline of the implant is derived, all data point values in the matrix of data points inside the curve thus defined are defined and tagged to be implant, at step 82. This, in essence, isolates all the implant values from the values derived from the areas of soft tissue and bone. The values thus defined as implant are then highlighted for the ultimate display at step 84 and are excluded from further data analysis to save processor time. A manual override is provided so that correction for misapplication of the implant defining procedure can be implemented by the operator if necessary.

Identify bone

Figure 4:
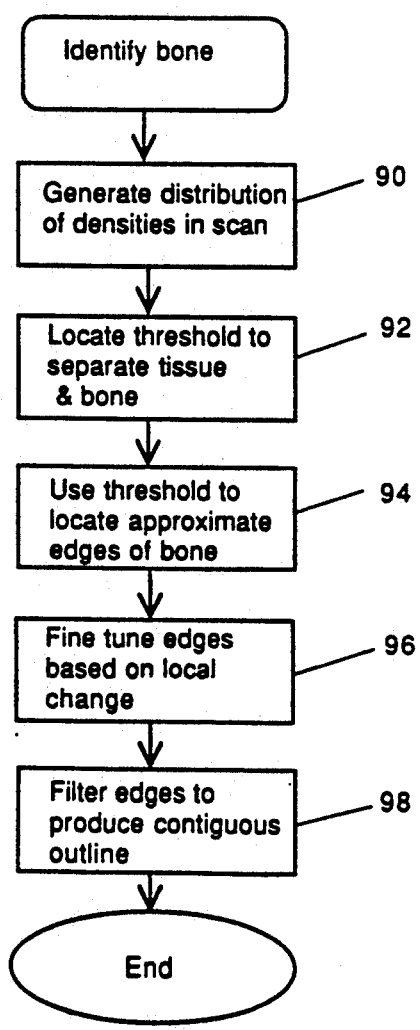
FIG. 4 is a flow chart showing the steps of the identify bone step from the flowchart of FIG. 2.

Now the matrix of PBM values has a set of values which correspond only to bone and tissue, and these two must be discriminated. To determine the edge of the bone, a raw threshold determination, such as that used for finding the edge of the implant, was found not to be accurate due to wide variations in the bone densities of actual patients, particularly at the bone margins and, in some cases, in the middle. Therefore a more sophisticated technique was adopted which begins with an edge detection procedure. The whole process is illustrated in FIG. 4, which corresponds to step 54 of FIG. 2.

In step 90, a density distribution curve of the values over the entire curve is generated. This curve is a plot of all PBM data values, regardless of location. The curve is examined at step 92 to find the first valley in the curve, which is the starting point for the threshold value to separate bone and soft tissue. This threshold is then used at step 94 to locate the approximate edges of the bone. The edges are then refined at step 96 through a process of locating where the change of PBM values between adjacent data points is large and still adjacent to the expected edge of the bone. Since the edge of the bone is expected to be contiguous, a median filter process is used at step 98 to finally adjust the bone edges. The edges thus defined are used to separate bone from soft tissue for the remainder of the analysis. Again a manual override is provided for the operator to correct for anomalous conditions.

Locate landmarks

Figure 5:
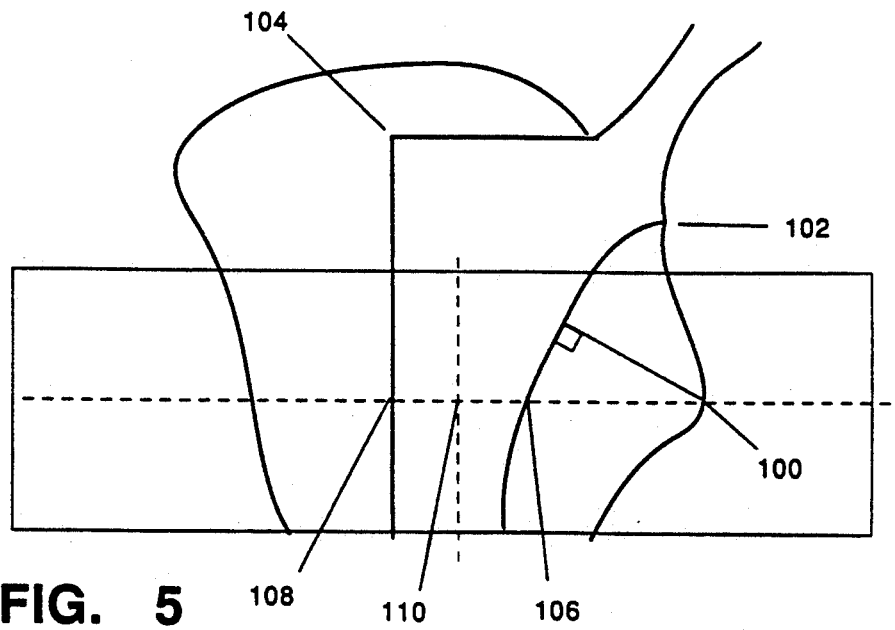
FIG. 5 is an illustration of the location of the landmarks in the femur and implant used in the process of FIG. 2.

As indicated by process block 56, up to six landmarks are identified from the bone edges and the prosthetic implant edges as previously described. The landmarks to be identified are illustrated in FIG. 5 and are: a) the lesser trochanter 100, b) the implant lip 102, c) the top of the implant 104, d) the medial edge 106 of the shaft of the implant, e) the lateral edge 108 of the shaft of the implant, and e) the center 110 of the shaft of the implant. These landmarks are located by comparative analysis of local data matrix values to identify the local value relationships that are characteristic of these landmarks. These landmarks serve as fiducial points, as will be described, for ensuring that subsequent scans of the patient will be properly aligned and thus may be directly compared to other such scans.

In the preferred embodiment of this process, the most medial tip of the lesser trochanter 110 is used as the origin point of a coordinate system to divide the samples of the data matrix, by ray coordinates, into the five regions, as indicated in process step 70 of FIG. 2. The location of the lesser trochanter is defined by the system to be the medial bone edge that is farthest from the implant in a plane perpendicular from the implant edge. This is illustrated in FIG. 5 where a perpendicular line is drawn from the trochanter perpendicular to the implant edge, and the lesser trochanter is shown at 100. Also in FIG. 5, a horizontal dashed line is drawn on the scan line of the trochanter as well.

The implant lip 102 is defined as the first line of the scan (y-coordinate) where there is no bone found on the medial side of the implant. This is the point at which the inside edge of the implant exits the bone.

The top of the implant 104 is defined at the first line of the scan (y-coordinate) in which the lateral or outside edge of the implant boundary has an abrupt horizontal change.

The medial 106 and lateral 108 edge of the implant are defined at the horizontal line (y-coordinate) of the trochanter. In the matrix of values, the position of the coordinates of the edges of the bone on the same scan line (the horizontal dashed line in FIG. 5) as the trochanter was defined are used. The shaft centerline 110 is defined as the point halfway in between the medial and lateral edge of the implant shaft.

The lesser trochanter, the medial edge, the lateral edge, and the centerline are all used for positioning the regions described below. The implant top and the tip of the implant are used for the forced nodes in the implant isolation and curve fitting routine already described above.

Locating regions

The fiducial points thus derived are then used to define the useful regions or interest for examination of bone density adjacent the implant, as illustrated at step 58 of FIG. 2. In the present instrument embodying the invention, at least four such regions are identified.

The first of these regions is a baseline region, which is intended to provide a set of samples that are free from artifacts and bone, and that may be used to standardize the PBM values from scan to scan despite variations in soft tissue, x-ray intensity, and detector sensitivity. The baseline region is defined beginning at the lesser trochanter. The medial edge of the baseline regions is defined as a vertical line located 1.5 cm medially from the lesser trochanter. At the same horizontal position (the same y-coordinate), the lateral edge of the baseline region is defined to be 1.0 cm lateral from the lateral edge of the implant. The upper and lower (distal and proximal) edges of the baseline region are defined as 2 cm distal and proximal from the lesser trochanter, for a total vertical extent of 4 cm. A rectangular solid line is drawn on FIG. 5 illustrating the area of the baseline region.

A second region is a medial inferior region extending from the trochanter proximally by 2 cm and medial to the implant edge, and incorporating the area of bone located within that region. This region would thus lie within the baseline region, and would incorporate all the area of bone medial to the implant, inside the baseline area and below the horizontal of the lesser trochanter.

A third region is a medial superior region extending from the trochanter proximally 2 cm and medial to the implant edge. Again this region is in the baseline region, and would incorporate all the area of bone medial to the implant, inside the baseline area and above the horizontal of the lesser trochanter.

A fourth region is the first lateral region beginning at the horizontal (y-coordinate) level of the trochanter and proceeding proximally 2 cm on the lateral side of the implant. This area would thus be all the bone area lateral to the implant, inside the baseline area, and above the horizontal to the trochanter.

A fifth region is the second lateral region beginning at the proximal edge of the last region and proceeding an additional 2 cm up or proximally. This last regions would include an area of bone outside the baseline region, lateral to the implant edge, and extending 2 cm upward from the fourth region above.

Referring to process block 60, the baseline value is now calculated. A curve of the distribution of PBM values throughout the baseline region is made. An initial value is selected which is the most prevalent value in the curve, or the peak of the distribution. The initial value is adjusted by an iterative process converging onto the average value of the most common tissue in the region of interest. The region of interest here, the baseline region, was selected so be of such a size and location that soft tissue, i.e. not bone or implant, would be the prevalent tissue in the area.

Display

Figure 8:
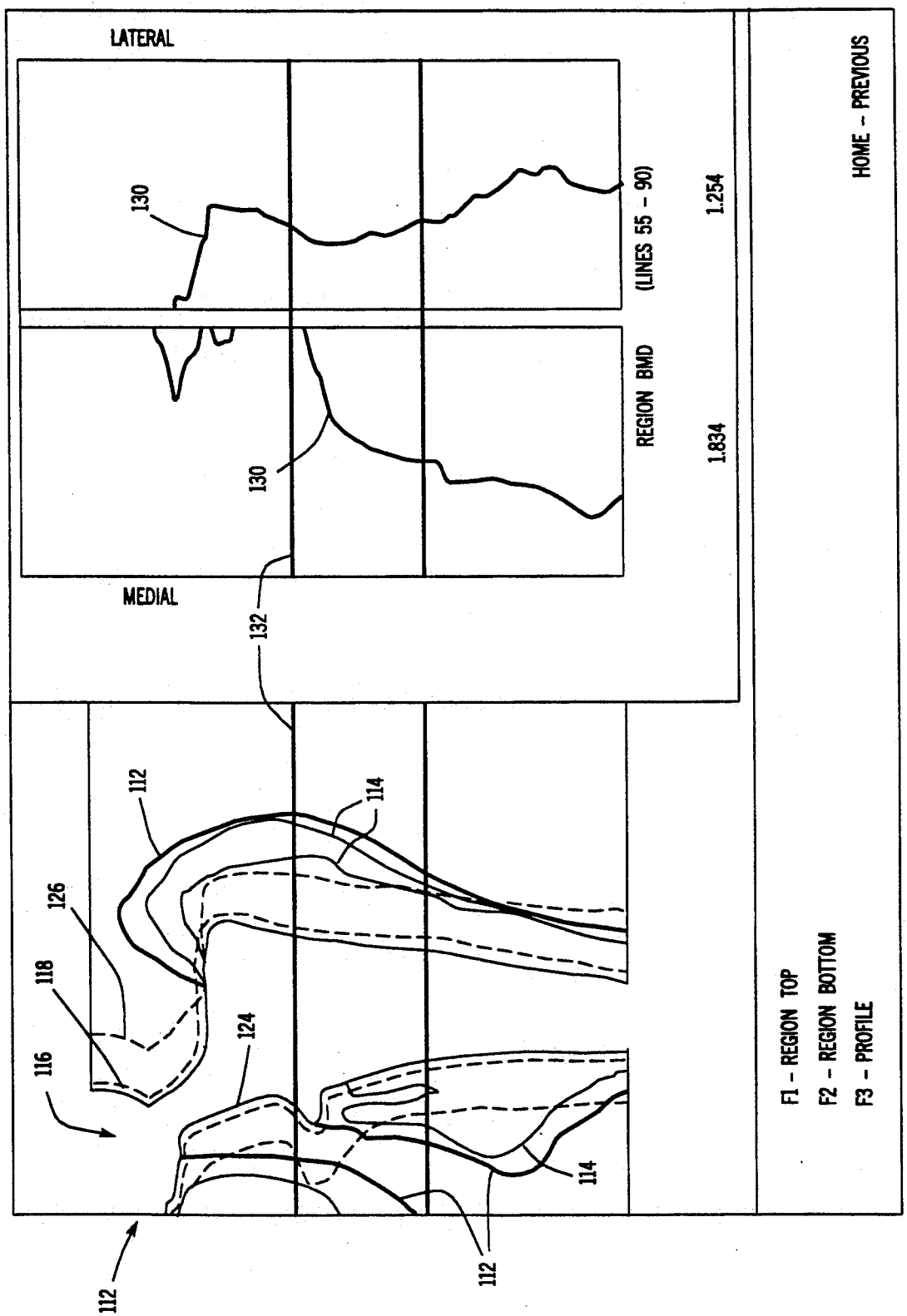
FIG. 8 is a pictorial representation of a screen display of a bone density image together with a periprosthetic histogram.
Figure 9:
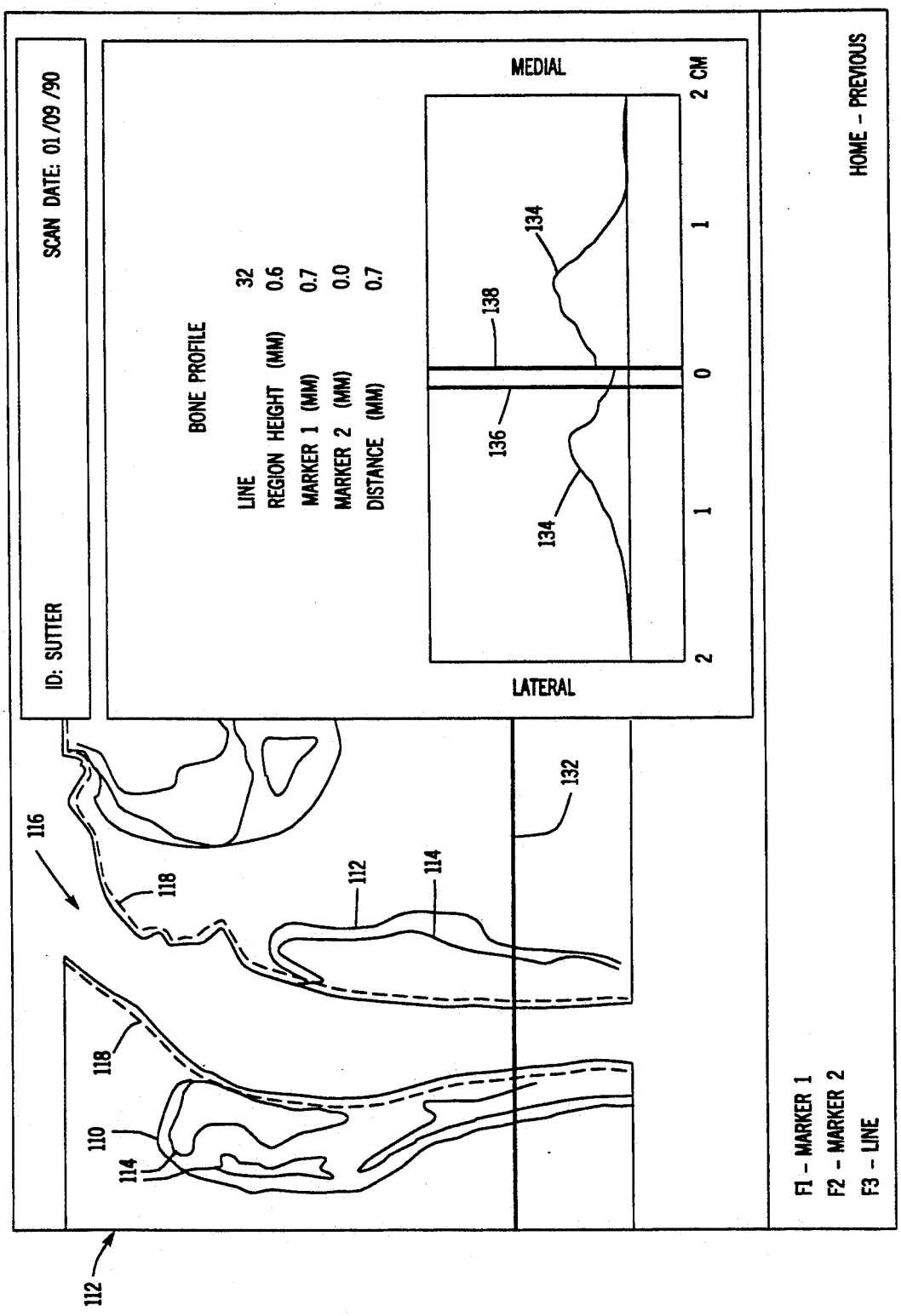
FIG. 9 is a pictorial representation of s screen display of a bone density image together with a transprosthetic profile.

The data matrix may be displayed as a bone density image is represented in step 62 and sample display are shown in FIGS. 8 and 9. The displays are composed of pixels whose coordinates on the display correspond to the coordinates of rays 16 associated with the samples pairs of the data matrix. The intensity of each pixel in the defined area of bone is made proportional to the PBM, and hence the BMD, along the corresponding ray 16. The pixels will thus qualitatively delineate the edge 112 of the femur 26, and the boundaries 114 of different bone density, by their intensity. As referred to hereafter and by convention, the long axis of the femur 26, and hence the y-axis of the scan, is oriented vertically in the bone density image 122 with the proximal end of the femur 26 toward the top of the bone density image 122 and the distal end of the femur 26 toward the bottom of the bone density image 122 as would mirror a standing person.

The pixels having associated matrix elements with PBM values identified to the prosthetic implant are set equal to a background color to form a silhouette 116 of the prosthesis on the bone density image 122 readily distinguishable from the image of the femur 26. The pixels corresponding to elements of the data matrix along the edge between the prosthetic implant 27 and other tissue are shown on the display 42 as a red line (dotted on FIGS. 8 and 9). These pixels and their corresponding data matrix elements will be termed the implant boundary 118. The operator may correct or adjust the implant boundary 118 as automatically defined above, by use of commands entered via the keyboard 38 and the trackball 40. Such adjustments, when necessary, will be performed in areas of the implant boundary 118 near sharp corners in the prosthetic implant 27 where the algorithmic curve fitting process has performed poorly.

The bone mineral composition ("BMC"), the total area of bone and the BMD are calculated for each of these four above described regions of interest from the previously obtained PBM values: the medial and lateral, superior and inferior regions, all calculated relative to the baseline value. These areas are chosen to provide a general measure of bone characteristic that may be used for patient to patient comparison. For the purpose of this calculation, samples that fall only partially within the regions defined above only contribute a fraction of their calibrated PBM values to the measurements for the regions in proportion to the fraction of their total area within that region. These values are used to generate the shading information for the pixels of FIGS. 8 and 9.

Note that all definition of regions of interest are calibrated from fixed fiduciary locations on the bone of the patient. This feature permits the instrument to be repeatedly used over time to measure changes in bone density at the fixed prescribed regions of interest.

Periprosthetic histogram

Figure 6:
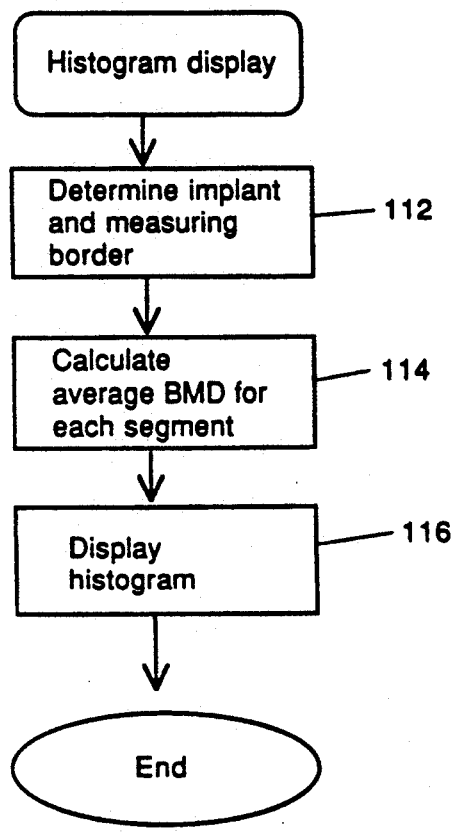
FIG. 6 is a flow chart showing the steps of creating a histogram of bone density.

The BMD values near the prosthetic implant 27 may be displayed in histogram or profile form as will now be described. Referring to the flowchart of FIG. 6, a density histogram may be prepared for the femur 26 having the prosthetic implant 27. The density histogram is described in conjunction with the display illustrated in FIG. 8.

At process step 112, a measurement boundary 126 (shown in FIG. 8) offset from the medial and lateral edges of the prosthetic implant 27 is identified. The measurement boundary 126 is set equal to the y coordinates of the implant boundary 124, the definition of which was previously described, with a predetermined horizontal width added to x-coordinates of the implant boundary 124. If desired, the measurement area can be offset from the implant boundary, so that the measurement area effectively includes the area between, for example, 3 and 10 mm away from the implant edge, rather that measuring beginning at the implant boundary edge, i.e. from 0 to 10 mm.

Referring to FIG. 8, the measurement boundary 126 is displayed on the bone density image 122 by a red line (dotted in FIG. 8) at the coordinates of the display corresponding to the y coordinates of the matrix elements of the measurement boundary 126. The width of the measurement boundary 126 from the implant boundary 124 may vary between 2 to 10 mm, as selected by the operator. One measurement boundary 126 is associated with each of the medial and lateral implant boundaries 124 and is horizontally extending in a direction away from the prosthetic implant 27. If desired, but not shown in FIG. 8, the measurement area can be offset horizontally from the implant edge a distance of up to 3 mm.

A series of vertically adjacent and horizontally extending segments may be defined within the zone between the measurement and implant boundaries 126 and 124, following the convention that the y axis of the data matrix is vertical and the x-axis is horizontal. Each of these segments may may contain from 1 to 10 samples or scan lines of the data matrix and as wide as the number of samples contained between the measurement and implant boundaries 126 and 124. The average BMD value for each segment is calculated at process block 114. At process block 116 the calculated values of BMD are plotted on a histogram 130 shown in FIG. 8, having average BMD on one axis and on the other axis distance from a reference point corresponding approximately to distance along the prosthetic implant 27 as a result of the alignment of the prosthetic implant 27 with the y-axis. One histogram 130 is created for the medial side of the prosthetic implant 27 and one for the lateral side of the prosthetic implant 27. The two histograms 130 are arranged to share their y-axis axes to provide ready comparison of the medial and lateral sides and hence to indicate visually symmetrical stress effects as have been described together to give a indication of the periprosthetic bone quality.

Two horizontal marker lines 132 superimposed on the bone density image 122 at arbitrary y-axis values, determined by the operator and on the corresponding y axis values of the histograms 130, may be used to identify a number of segments. The average bone density value of the segments so identified may be computed and displayed numerically on display 42. The index numbers of the scan lines between the marker lines 132 as referenced from the origin point are also displayed. Thus, the average bone density over a given length of the interface between the femur 26 and the prosthetic implant 27 may be quantified at any given location as desired by the operator.

Transprosthetic Profile

Figure 7:
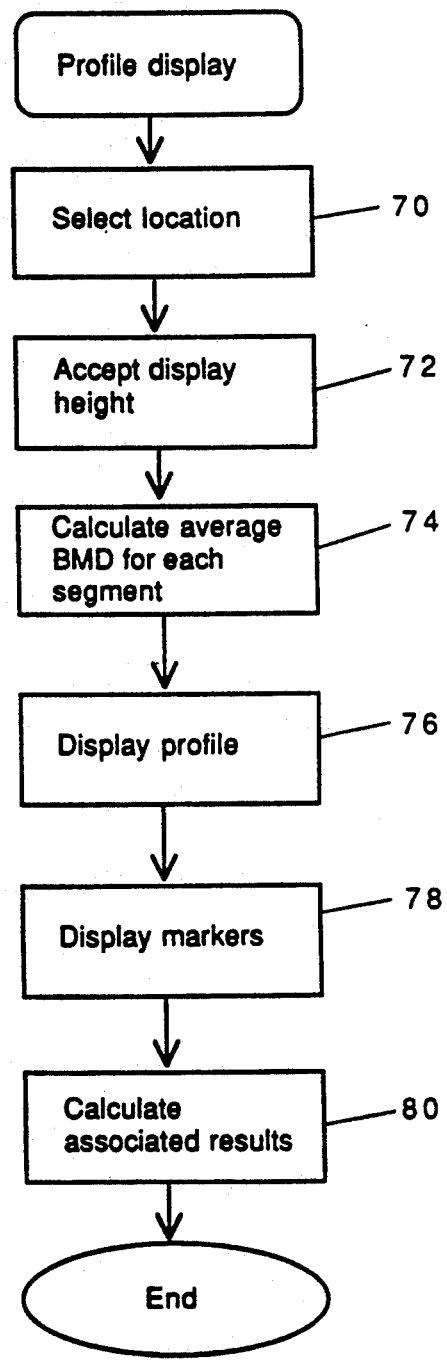
FIG. 7 is a flow chart showing the steps of creating a transprosthetic profile of bone density

Alternatively, a profile of bone density may be generated for elements of the data matrix along one scan line. Referring to the flowchart of FIG. 7 and shown in the profile display of FIG. 9, a single horizontal marker line 132 of a predetermined height may be used to identify a single selected scan line of data in the data matrix at process step 70. This data is plotted as a profile 134 at that selected height or location, by process step 72, showing BMD versus x-axis position, where the x-axis, as has been described, is directed so that the profile is transprosthetic. The implant itself is not shown in the display of FIG. 9. Both the lateral and medial sides of the scan line are shown in the profile 134, and the vertical location of the profile 134 is determined at process step 74 to be the BMD at each location. The process step 76 indicates that the display of FIG. 9 is generated and produced on the display 42. A pair of markers 136 and 138 may be positioned along and perpendicular to the x-axis axes of the profile 134 to allow the operator to measure absolute distance from the medial or lateral edge of the prosthetic implant 27 to that marker 136 or 138, and hence to that portion of the profile 134. Process step 78 represents the step of displaying the markers. The absolute position of the markers is shown in numerical form on display 42 by process block 80. This quantitative measure aids in evaluating bone resorption at specific locations along the implant, a measurement that was previously performed with radiographs and a ruler and with considerably less accuracy.

Although the above description of the transprothestic profile is described with respect to a single scan line, it should be understood that more than one scan line could be in the profile region. If this is the case, the method is followed as above except that a mean is calculated of the values in the scan lines in the region and the mean values are presented in the display.

The above description has been that of a preferred embodiment of the present invention. It will occur to those who practice the art that many modifications may be made without departing from the spirit and scope of the invention. In order to apprise the public of the various embodiments that may fall within the scope of the invention, the following claims are made.

We claim:

1. A method of using a dual energy densitometer having a visual display to determine bone mineral density in a patient having a bone with a prosthetic implant, the method comprising the steps of:

a) scanning with said dual energy densitometer said patient in the region of said bone and said implant so as to generate a two dimensional matrix of data elements wherein the value of each said data element of said matrix is proportional to the absorption of energy by said bone and implant at a defined location in the internal structure of said patient in said region, the matrix holding a corresponding location and data value for each data element;

b) analyzing the matrix of data elements to identify a data element as a boundary data element, the boundary data element being on an edge of said implant adjacent to a portion of the bone of the patient, the location of said boundary data element being a function of a value and location of the boundary data element and a value and location of at least one immediately adjacent data element;

c) using a plurality of the boundary data elements to form an implant boundary;

d) establishing a measurement boundary which conforms to said implant boundary and is translated from said implant boundary by a predetermined distance along a translation axis;

e) calculating bone mineral density within a plurality of segments contained between the implant boundary and the measurement boundary and displaced along the implant boundary to produce a set of segment values indicative of the density of the bone adjacent to said implant; and f) displaying on said visual display a plot of segment values versus distance along the implant boundary.

2. The method of claim 1 including the step of analyzing the matrix of data elements to identify the position of a fiducial point of the bone within the matrix of data elements and referencing the plot of segment values to said fiducial point.

3. The method of claim 1 wherein said implant boundary conforms to the shape of said implant and isolates and removes from the calculation of bone density data elements resulting from absorption of energy by said implant.

4. The method of claim 1 wherein the implant has opposed medial and lateral edges and where the plot of segment values is composed of a medial and lateral histogram with corresponding segment values plotted along first axes and distance along the implant boundary plotted along second axes and where the second axes are aligned so that the corresponding medial lateral segment values are aligned.

5. A method of using a dual energy densitometer having a visual display to determine bone mineral density in a patient having a bone with a prosthetic implant, the method comprising the steps of:

a) scanning with said dual energy densitometer said patient in the region of said bone and said implant so as to generate a two dimensional matrix of data elements wherein the value of each said data element of said matrix is proportional to the absorption of energy by said bone and implant at a defined location in the internal structure of the patient in said region, the matrix holding a corresponding location and data value for each data element;

b) analyzing the matrix of data elements to identify a data element as a boundary data element, the boundary data element being on an edge of said implant adjacent to a portion of the bone of the patient, the location of said boundary data element being a function of a value and location of the boundary data element and a value and location of at least one immediately adjacent data element;

c) using a plurality of the boundary data elements to form an implant boundary d) identifying the position of a fiducial point of the bone within the matrix of data elements;

e) calculating bone mineral density along a measurement axis having a predetermined distance and orientation with respect to said fiducial point and including a portion of the bone adjacent said implant as defined by the implant boundary; and f) displaying on said visual display a plot of the bone mineral density along said measurement axis.

6. A method of using a dual energy densitometer having a visual display to determine bone mineral density in a patient having a bone with a prosthetic implant, the method comprising the steps of:

a) scanning with said dual energy densitometer said patient in the region of said bone and said implant so as to generate a two dimensional matrix of data elements wherein the value of each said data element of said matrix is proportional to the absorption of energy by said bone and implant at a defined location in the internal structure of said patient in said region, the matrix holding a corresponding location and data value for each data element;

b) analyzing the matrix of data elements to identify a data element as a boundary data element, the boundary data element being on an edge of said implant adjacent to a portion of the bone of the patient, the location of said boundary data element being a function of a value and location of the boundary data element and a value and location of at least one immediately adjacent data element;

c) using a plurality of the boundary data elements to form an implant boundary;

d) establishing a measurement boundary which conforms to said implant boundary and is translated from said implant boundary by a predetermined distance along a translation axis;

e) calculating bone mineral density for the data values located between the implant boundary and the measurement boundary and displaced along the implant boundary to produce a set of segment values corresponding to the density of the bone adjacent to the implant;

f) averaging the segment values to obtain a value representing average bone mineral density adjacent the implant; and g) displaying on said visual display a visual representation of the result of step f).

7. A method of using a dual energy densitometer having a visual display to determine bone mineral density in a patient having a bone with a prosthetic implant, the method comprising the steps of:

a) scanning with said dual energy densitometer said patient in the region of said bone and said implant so as to generate a two dimensional matrix of data elements wherein the value of each said data element of said matrix is proportional to the absorption of energy by said bone and implant at a defined location in the internal structure of said patient in said region, the matrix holding a corresponding location and data value for each data element;

b) analyzing the matrix of data elements to identify a data element as a boundary data element, the boundary data element being on an edge of said implant adjacent to a portion of the bone of the patient, the location of said boundary data element being a function of a value and location of the boundary data element and a value and location of at least one immediately adjacent data element;

c) using a plurality of the boundary data elements to form an implant boundary;

d) employing the implant boundary to isolate and remove from the determination of bone mineral density data elements resulting from energy absorbed by said implant;

e) employing the implant boundary to identify those data elements which result from energy absorbed by bone immediately adjacent said implant;

f) displaying on said visual display a visual representation of said matrix showing said implant and said bone adjacent said implant;

g) analyzing the data elements identified in step e) to determine bone mineral density of said bone adjacent said implant; and h) displaying the result of step g) on said visual display.

8. A method as claimed in claim 7 further including a step for identifying within said matrix a fiducial point of the bone and referencing the data elements analyzed in step g) to said fiducial point.

9. A method of using a dual energy densitometer having a visual display to determine bone mineral density in a patient having a bone with a prosthetic implant, comprising the steps of:

a) scanning with said dual energy densitometer said patient in the region of said bone and said implant so as to generate a two dimensional matrix of data elements wherein the value of each said data element of said matrix is proportional to the absorption of energy by said bone and implant at a defined location in the internal structure of said patient in said region, the matrix holding a corresponding location and data value for each data element;

b) analyzing the matrix of data elements to identify a data element as a boundary data element, the boundary data element being on an edge of said implant adjacent to a portion of the bone of the patient, the location of said boundary data element being a function of a value and location of the boundary data element and a value and location of at least one immediately adjacent data element;

c) using a plurality of the boundary data elements to form an implant boundary;

d) locating at least one region of interest, said region of interest containing only bone data elements and having one side adjacent said implant boundary, said one side conforming to the shape of said adjacent implant boundary;

e) displaying on said visual display a visual representation of said bone, said implant and said region of interest;

f) analyzing said bone data elements within said region of interest to calculate bone mineral density within said region of interest; and g) displaying on said visual representation of said calculated bone mineral density corresponding to the bone mineral density of bone adjacent said implant in said region of interest.

10. The method as claimed in claim 9 further including the step of establishing at least one landmark on said edge boundary and using said landmark to locate at least one said region of interest.

11. A method of using a dual energy densitometer having a visual display to monitor change in bone density in bone adjacent a prosthetic implant, said method comprising the steps of:

a) scanning with said dual energy densitometer said bone and said implant so as to generate a two dimensional matrix of data elements wherein the value of each said data element of said matrix is proportional to the absorption of energy by said bone and implant at a defined location in the internal structure of said patient in said region, the matrix holding a corresponding location and data value for each data element;

b) analyzing the matrix of data elements to identify a data element as a boundary data element, the boundary data element being on an edge of said implant adjacent to a portion of the bone of the patient, the location of said boundary data element being a function of a value and location of the boundary data element and a value and location of at least one immediately adjacent data element;

c) using a plurality of the boundary data elements to form a first and second implant boundary generally opposed about an axis of the implant;

d) employing the first and second implant boundaries to isolate data elements associated with the implant from said other data elements so that said implant data elements are removed from the determination of bone mineral density;

e) analyzing said other data elements to identify bone data elements which result from energy absorbed by said bone;

f) defining a medial and lateral edge boundary between said bone data elements and non-bone data elements of said other data elements;

g) establishing at least one landmark on said edge boundary;

h) using said landmark to locate at least two regions of interest, one region of interest on the medial side of said implant and the other region of interest on the lateral side of said implant, each said region of interest containing only bone data elements and each said region of interest having one side adjacent said implant boundary, each said one side conforming to the shape of one implant boundary;

i) analyzing said bone data elements within each said region of interest to calculate bone mineral density within each said region of interest;

j) displaying on said visual display a comparison of said calculated bone mineral density for each said region of interest corresponding to the bone mineral density of bone adjacent said implant in each said region of interest; and k) repeating on a subsequent date steps a) through j) so as to determine the change in bone mineral density in each said region of interest with time.

12. A dual energy densitometer for determining bone mineral density in a patient having a bone with a prosthetic implant, comprising:

a) a means to scan said patient with said densitometer in the region of said bone and said implant so as to generate a two dimensional matrix of data elements wherein the value of each said data element of said matrix is proportional to the absorption of energy by said implant and bone at a defined location in the internal structure of said patient in said region, the matrix holding a corresponding location and data value for each data element;

b) means for analyzing the matrix of data elements to identify a data element as a boundary data element, the boundary data element being on an edge of said implant adjacent to a portion of the bone of the patient, the location of said boundary data element being a function of a value and location of the boundary data element and a value and location of at least one immediately adjacent data element;

c) means using a plurality of the boundary data elements for forming an implant boundary;

d) means using the implant boundary to distinguish within said matrix, data elements which result from the absorption of energy by said bone from data elements which result from the absorption of the implant;

e) a means to establish at least one region of interest, said one region of interest containing only bone data elements resulting from energy absorbed by bone immediately adjacent said implant boundary;

f) a means to visually display said matrix so that the region of the matrix containing implant data elements is highlighted and conforms to the shape of said implant, and so that said value of each said bone data element is converted to an intensity of light such that the intensity of light is proportional to the absorption of energy by said bone, and so that the region of matrix containing bone data elements conforms to the shape of said bone, and so that at least one region of interest is able to be identified;

g) a means to analyze bone data elements in said one region of interest so as to determine bone mineral density;

h) a means to visually display a representation of bone mineral density in said one region of interest.

* * * * *